(12) United States Patent
Kuechler et al.

(10) Patent No.: US 7,007,701 B2
(45) Date of Patent: Mar. 7, 2006

(54) PROCESSOR FOR REMOVING CONTAMINANTS FROM A COMPRESSOR IN A METHANOL TO OLEFIN SEPARATION SYSTEM

(75) Inventors: Keith H. Kuechler, Friendswood, TX (US); David R. Lumgair, Craddockville, VA (US); Nicolas P. Coute, Houston, TX (US); Paul N. Chisholm, Houston, TX (US); Cor F. Van Egmond, Pasadena, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 383 days.

(21) Appl. No.: 10/280,368

(22) Filed: Oct. 28, 2002

(65) Prior Publication Data

US 2004/0079392 A1 Apr. 29, 2004

(51) Int. Cl.
*B08B 9/00* (2006.01)
(52) U.S. Cl. ............... 134/22.19; 134/22.1; 134/22.18
(58) Field of Classification Search ............... 134/22.1, 134/22.22, 22.18, 22.19
See application file for complete search history.

(56) References Cited

U.S. PATENT DOCUMENTS

| 4,076,796 A | 2/1978 | Reh et al. ............... 423/659 |
| 4,667,242 A | 5/1987 | Hagino ................. 358/174 |
| 4,677,242 A | 6/1987 | Kaiser ................. 585/638 |
| 5,952,538 A | 9/1999 | Vaughn et al. ............ 585/640 |
| 6,046,373 A | 4/2000 | Sun .................... 585/640 |
| 6,051,746 A | 4/2000 | Sun et al. ............... 585/639 |
| 6,121,504 A | 9/2000 | Kuechler et al. ......... 585/640 |
| 6,166,282 A | 12/2000 | Miller .................. 585/638 |
| 6,287,522 B1 | 9/2001 | Lomas ................. 422/144 |
| 6,441,261 B1 | 8/2002 | Kuechler et al. ......... 585/639 |
| 6,444,869 B1 | 9/2002 | Senetar et al. ............ 585/809 |
| 2004/0267075 A1 * | 12/2004 | Lumgair et al. .......... 585/639 |

FOREIGN PATENT DOCUMENTS

| JP | 49026241 | 3/1974 |
| RO | 81748 | 6/1983 |
| SU | 1719112 | 3/1992 |

OTHER PUBLICATIONS

U.S. Appl. No. 09/564,613, filed May 4, 2000, Godwin et al.
U.S. Appl. No. 09/708,753, filed Nov. 8, 2000, Lattner et al.
Kunii et al., Fluidization Engineering, Robert E. Krieger Publishing Company, New York, New York, (1977).
Boyce., "Compressors", Perry's Chemical Engineers' Handbook, (7th Ed.) pp. 10-57, (1997).
Othmer et al., Riser Reactor, Fluidization and Fluid-Particle System, Reinhold Publishing Corporation, New York, 1960. pp. 48-59, (1960).

* cited by examiner

Primary Examiner—Zeinab El-Arini

(57) ABSTRACT

The invention is to a process for removing contaminants from a compressor and/or compressor intercooler in a methanol to olefin separation system. The process comprises compressing an effluent in a compressor having an inlet and an outlet and a compressor surface, the compressing occurring under conditions effective to form a contaminant on the compressor surface. A contaminant-removal medium is injected into the compressor or intercooler and the contaminant-removal medium contacts the contaminant under conditions effective to remove the contaminant from the compressor or intercooler inner surface thereby forming a mobile contaminant. The mobile contaminant is then removed from the compressor or intercooler.

44 Claims, 2 Drawing Sheets

PROCESSOR FOR REMOVING CONTAMINANTS FROM A COMPRESSOR IN A METHANOL TO OLEFIN SEPARATION SYSTEM

FIELD OF THE INVENTION

The present invention relates to a process and system for reducing compressor fouling. More particularly, the invention is directed to injecting a contaminant-removal medium into one or more compressors and/or intercoolers in a methanol to olefin separation system under conditions effective to remove contaminants from the internal surfaces thereof.

BACKGROUND OF THE INVENTION

Light olefins, defined herein as ethylene and propylene, serve as feeds for the production of numerous chemicals. Olefins traditionally are produced by petroleum cracking. Because of the limited supply and/or the high cost of petroleum sources, the cost of producing olefins from petroleum sources has increased steadily.

Alternative feedstocks for the production of light olefins include oxygenates. In an oxygenate to olefin (OTO) reaction system, a feedstock containing an oxygenate is vaporized and introduced into a reactor. Exemplary oxygenates include alcohols such as methanol and ethanol, dimethyl ether, methyl ethyl ether, methyl formate, and dimethyl carbonate. In a methanol to olefin (MTO) reaction system, which is a type of OTO reaction system, the oxygenate-containing feedstock includes methanol. In the reactor, the methanol contacts a catalyst, preferably a molecular sieve catalyst, under conditions effective to create an product effluent comprising desirable light olefins.

The product effluent from an MTO reaction system is then directed to a separation system including one or more separation devices, which are well known in the art. The separation system separates the desirable light olefins from other components in the product effluent such as unreacted feed and undesirable byproducts. MTO separation systems typically include one or more compressor units or bodies, which are adapted to compress at least a portion of the product effluent. The compressors have the dual purpose of facilitating the movement of the product effluent through the separation system as well as condensing out heavier less-desirable components from the product effluent.

Compressors such as centrifugal compressors are often formed of a body having one or more stages. Each stage has a respective inlet and outlet and usually includes one or more sections, each having an impeller and a diaphragm. In many instances, multiple bodies and stages are used. To reduce the power required to drive these multiple stages, intercoolers are often placed between them. An intercooler is a heat exchanger situated immediately downstream from a compressor. In some cases, intercoolers are also used between stages to reduce the power required for compression.

Compressor fouling may occur in compressors or intercoolers found in an MTO separation system. Fouling is the build up of a solid, e.g., crystal, or a layer of liquid hydrocarbon contaminants within a compressor or intercooler. For example, the liquid contaminants may form through polymerization within the compressor body. Compressor fouling in an MTO separation system is undesirable because as contaminants build up inside the compressor, imbalances may develop causing vibrations, compressor inefficiency and, ultimately, compressor failure. Contaminants also may solidify or condense in the compressor intercoolers. Fouling in compressor intercoolers is undesirable because heat transfer is impaired and flow rate is reduced.

It is therefore desirable to have a process for removing contaminants that have accumulated on the internal surfaces of compressors and intercoolers in an MTO separation system.

SUMMARY OF THE INVENTION

In one embodiment, the present invention is directed to a process for removing contaminants from a compressor in a methanol to olefin (MTO) separation system. The process includes compressing an effluent in the compressor, the compressor having an inlet and an outlet and an inner compressor surface. The compressing occurs under conditions effective to form a contaminant on the inner compressor surface. A contaminant-removal medium is injected into the compressor, and the contaminant-removal medium contacts the contaminant under conditions effective to remove the contaminant from the inner compressor surface thereby forming a mobile contaminant. The mobile contaminant is then removed from the compressor.

Another embodiment of the invention is a process for compressing an effluent withdrawn from a MTO conversion apparatus. The process comprises contacting a methanol-containing feedstock with a catalyst under conditions effective to form a product effluent comprising light olefins. At least a portion of the product effluent is directed to a compressor having a compressor surface. The at least a portion of the product effluent is compressed in the compressor under conditions effective to form a deposit on the compressor surface. A deposit-removal medium contacts the deposit under conditions effective to remove the deposit from the compressor surface.

The invention is also directed to a compressor in a MTO separation system. The compressor includes a compressor body forming a compressor inlet for receiving an effluent to be compressed, the compressor inlet being in fluid communication with a reactor outlet. The compressor body also forms a compressor outlet. A compressing mechanism within the compressor body acts to compress the effluent. An injection unit is also provided having at least one nozzle for injecting a deposit-removal medium into the compressing mechanism.

In another embodiment, the invention is a process for removing contaminants from a compressor intercooler in a MTO separation system. In this embodiment, an effluent is compressed in a compressor to form a compressed effluent. The compressed effluent is cooled in a compressor intercooler having an inner surface under conditions effective to form a contaminant on the inner surface. A contaminant-removal medium is injected into the intercooler and contacts the contaminant under conditions effective to remove the contaminant from the inner surface thereby forming a mobile contaminant. The mobile contaminant is then removed from the intercooler.

The invention is also directed to a process for removing contaminants from a compressor in a MTO separation system. In this embodiment, an effluent is compressed in a first compressor stage to form a compressed effluent. The first compressor stage has a first inlet, a first outlet and a first inner compressor surface, and is in the compressor. The compressing occurs under conditions effective to form a contaminant on the first inner compressor surface. A contaminant-removal medium is injected into the first compressor stage and contacts the contaminant under conditions effective to remove the contaminant from the first inner compressor surface thereby forming a mobile contaminant. The mobile contaminant is then removed from the first compressor stage. Optionally, this process also includes compressing the compressed effluent in a second compressor stage, the second compressor stage having a second inlet, a second outlet and a second inner compressor surface. The first and second compressor stages may be in a single compressor body or in separate compressor bodies.

BRIEF DESCRIPTION OF THE DRAWINGS

Various embodiments of the overall invention are shown by way of example in the attached Figures, wherein.

DETAILED DESCRIPTION OF THE INVENTION

Figure 1:
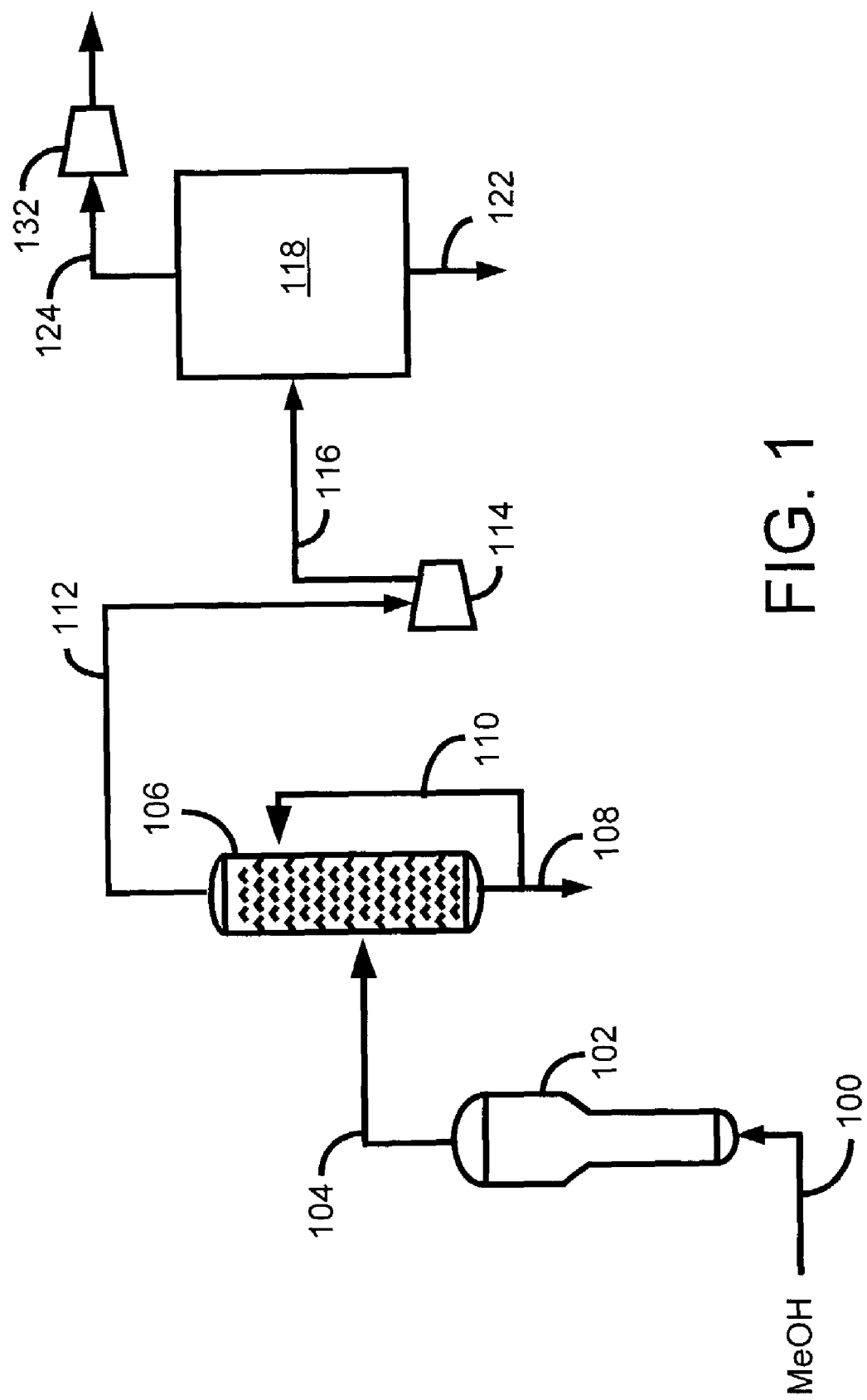
FIG. 1 is a flow diagram showing a process for reacting methanol to form a product effluent, which is directed to a Quench Tower and at least partially compressed.

This invention provides a process for removing contaminants that have accumulated on the internal surfaces of compressors and intercoolers in an MTO separation system. By removing these contaminants from the internal surfaces of one or more compressors or intercoolers in an MTO separation system, the efficiency and run time between off line cleanings of MTO separation system compressors can be increased and intercooler efficiency can be increased. In one embodiment, the process includes injecting a contaminant-removal medium into the compressor and contacting the contaminant-removal medium with the contaminant under conditions effective to form a mobile contaminant. The mobile contaminant is then removed from the compressor. The contaminant-removal medium can then be separated from the MTO product effluent through well known separation techniques such as by distillation or by using a knock-out or discharge drum.

Additionally or alternatively, the inventive process includes injecting the same or different contaminant-removal medium into an intercooler and contacting the contaminant-removal medium with the intercooler contaminant under conditions effective to form a mobile contaminant. The mobile contaminant is then removed from the intercooler. The contaminant-removal medium can then be separated from the MTO product effluent through well known separation techniques such as by distillation or by using a knock-out or discharge drum.

Through Gas Chromatography and Flame Ionization Detection (GC/FID) and Gas Chromatography and Mass Spectrometry (GC/MS) analysis techniques, various contaminants have been observed in the reactor effluent of the MTO process. In one specific reactor and catalyst system, hydrocarbons, particularly alkylated benzenes, formed the majority of the fouling contaminants. These hydrocarbon contaminants were found floating on an aqueous layer in a phase separation pot, e.g., a knock out drum. In this particular system, approximately 70 percent of the hydrocarbon contaminants found were C9, C10, C11 and C12 aromatic compounds. In addition to liquid hydrocarbon contaminants, yellowish rust-colored crystals had accumulated at the interface between the aqueous and hydrocarbon layers. These crystals were found to have been formed mostly of hexamethyl benzene (41 weight percent) with a freezing point of 330.8° F. (166° C.) and alkylated naphthalene with five carbon atoms (23 weight percent). The balance of the crystals were found to have been formed of multiply-alkylated benzenes and naphthalenes. Fouling also is believed to result from the polymerization of unsaturates, the condensation of unsaturates and oxygenates, as well as catalyst fines or salts mixed with heavy materials forming viscous immobile materials. A non-limiting list of potential fouling precursor compounds, which may be present in the effluent stream, includes butadiene, pentadiene, naphthalene, cyclopentadiene, hexadiene, cyclohexadiene, C7+ dienes, styrene, C4+ styrenic compounds, and mixtures thereof. A non-limiting list of potential fouling compounds, which also may be present in the effluent stream or which may be formed from one or more of the fouling precursor compounds, includes methyl acetylene, hexamethyl benzene, durene, and mixtures thereof. Fouling compounds or contaminants may form on one or more inner surfaces of a compressor or intercooler as an adherant, a residue, a film, a layer or a solid.

To remove these and other contaminants from the inner surfaces of MTO compressors, the invention provides for the injection of a contaminant-removal medium directly into one or more compressors and/or intercoolers. In one embodiment, the contaminant-removal medium is injected directly into one or more stages of a compressor body. Each stage in a centrifugal compressor includes an inlet, an outlet and one or more impellers partially surrounded by one or more diaphragms or walls that form a labyrinth. Preferably, one or more holes are drilled into the outer wall of a compressor adjacent a compressor stage and an atomizing nozzle or other injection device is inserted therein and securely attached thereto, e.g., by brazing, welding, mechanical means, or other securing method. In one embodiment, the injection device is welded with a flange near the injection point to facilitate cleaning of the injection device. Optionally, the compressor or intercooler is manufactured having holes in its outer surface adapted for receiving an injection nozzle, thereby not necessitating drilling into the outer surface of the compressor or intercooler. Preferably, each stage includes at least one injection nozzle and more preferably at least two injection nozzles. In this embodiment, the contaminant-removal medium is injected directly where the majority of the fouling contaminants are formed. In another embodiment, each stage section, having an impeller and a diaphragm, has one, two, or more than two contaminant-removal medium injection nozzles associated therewith.

Additionally or alternatively, one, two, or more than two holes are drilled in the side of the compressor inlet. In this embodiment, the contaminant-removal medium injection nozzles preferably are inserted in the hole(s) adjacent of the compressor inlet and secured thereto. Optionally, the contaminant-removal medium is injected through a nozzle that is adjacent the compressor inlet directly into the compressor inlet.

Additionally or alternatively, the contaminant-removal medium is injected into one or more compressor intercoolers. Compressor intercoolers are heat exchangers located downstream of or between compressor bodies or stages. Ideally, the intercoolers are shell-and-tube type heat exchangers. In another embodiment, the intercoolers are plate-and-frame type heat exchangers. If the compression system includes a plurality of compressor bodies, it may be desirable to cool the compressed stream between compressor bodies in compressor intercoolers to facilitate condensation of the heavier products as well as to reduce the power required to drive the multiple bodies. As fouling contaminants have been found to form within these intercoolers, the injection of contaminant-removal medium into the inlet of the intercoolers reduces the occurrence of intercooler fouling.

Figure 2:
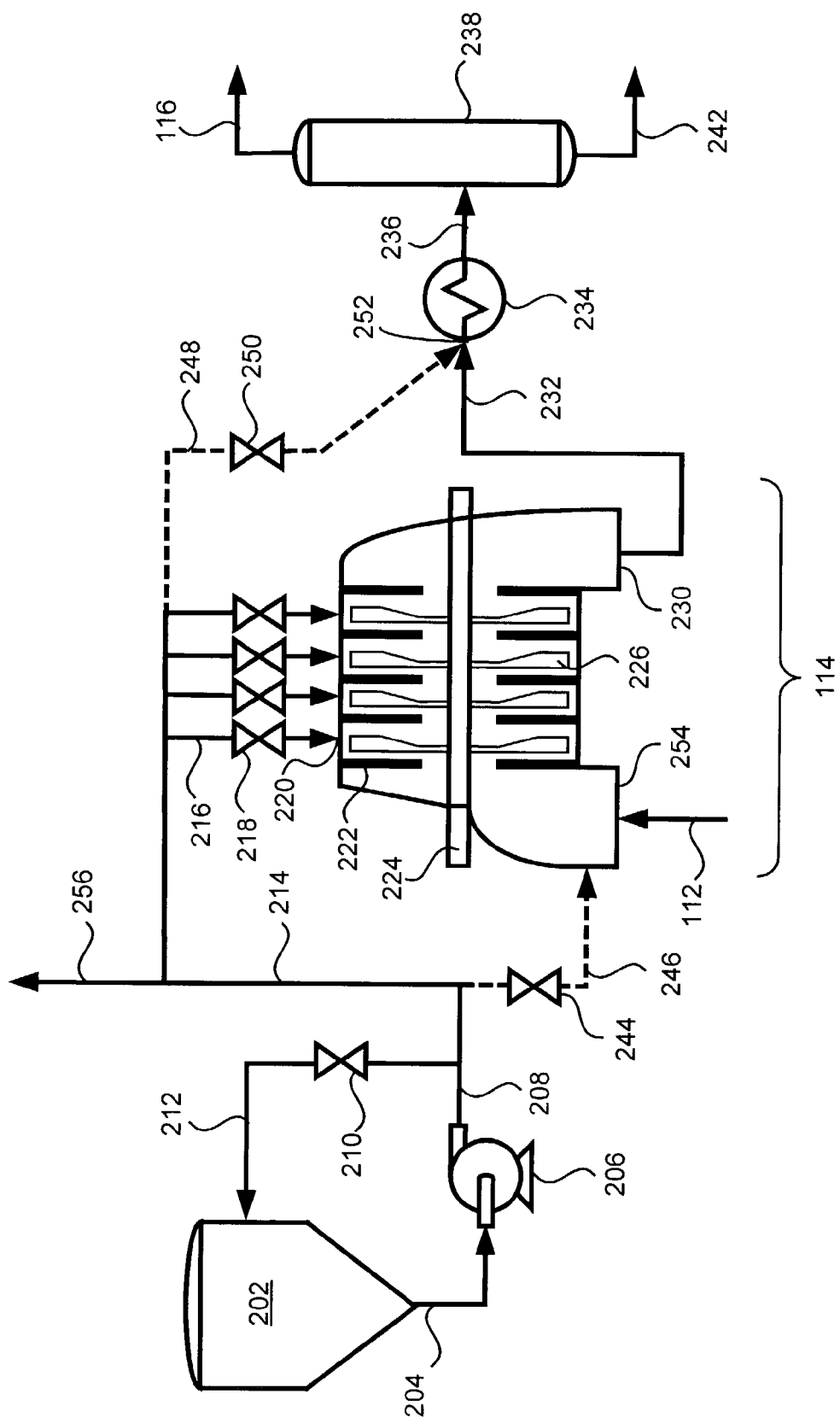
FIG. 2 is a flow diagram showing a compressor and injection system for removing fouling contaminants contained therein.

Typically, intercoolers are formed of an outer shell, which houses a first medium, and an inner tube, which passes through the shell and which houses a second medium. As the second material flows through the tube, heat is transferred between the first and second mediums. If the process gas is in the tube side of the intercoolers, as illustrated in FIG. 2, the contaminant-removal medium preferably is injected into the inlet head. If the process gas is in the shell side of the intercooler rather than the tube side of the intercooler, the contaminant-removal medium can be injected into the side of the intercooler as described above with respect to injecting contaminant-removal medium into the side of the one or more compressors. Preferably, each intercooler system is comprised of multiple parallel shells and often two or three banks of parallel shells in series.

While not wishing to be bound to any particular theory, it is believed that the contaminant-removal medium removes the fouling contaminants from the inner surfaces of the compressor by friction, e.g., sufficient force of the atomized contaminant-removal medium entering the compressor to shear the fouling contaminants from the inner surfaces thereof. Thus, in this embodiment, the contaminant-removal medium may be any liquid that is easily separated from the desired product, e.g., light olefins, in downstream processing, as discussed below, and that provides an adequate shearing force against the contaminants that have formed on the interior surfaces of the compressors and/or intercoolers. Additionally, by using a liquid aromatic compound as the contaminant removal medium, without being bound to any particular theory, it is believed that at least a portion of the fouling contaminants are dissolved in the removal medium and removed from the compressor through well known extraction principles in downstream processing, discussed in more detail below.

According to the present invention, a variety of contaminant-removal mediums may be implemented to remove these contaminants from the compressor and/or intercooler. Preferably, the contaminant-removal medium comprises an aromatic compound. Ideally, the contaminant-removal medium is a solution having at least 20 weight percent aromaticity, more preferably at least 50, at least 60, or at least 70 weight percent aromaticity, and most preferably at least 80 or at least 90 weight percent aromaticity based on the total weight of the contaminant removal medium. The contaminant-removal medium preferably is a wash oil boiling between 120° F. (48.9° C.) and 800° F. (426.7° C.), preferably between 200° F. (93.3° C.) and 700° F. (371.1° C.), and most preferably between 400° F. (204.4° C.) and 600° F. (315.5° C.). Optionally, the contaminant-removal medium is selected from the group consisting of: single ring aromatics (preferably non-aliphatic), multi-ring aromatics, aromatic naphthas, aromatic gas oils, and mixtures thereof. Heavy aromatic naphtha products used in oil field drilling are particularly desirable wash oils. In other embodiments, the contaminant removal medium comprises water. Preferably, the contaminant-removal medium comprises substantially no sulfur, although sulfur contained in an aromatic ring or a C5+ compound is tolerable in limited quantities. Preferably the contaminant-removal medium comprises less than 10000 wppm, preferably less than 100 wppm, more preferably less than 1 wppm, and most preferably an undetectable amount of sulfur, defined herein as less than 0.01 wppm sulfur. Heavy aromatics are preferably injected into the compressor over light aromatics, which are vaporized by the heat of compression, thereby reducing or eliminating the ability of the light aromatics to remove contaminants from the inner surfaces of the compressor. However, lighter aromatics containing single and double ring aromatics or mixtures of aromatics are used as the contaminant-removal medium provided the conditions at the injection point allow a portion of the injected wash oil to remain as a liquid. The lighter aromatics are preferred for washing discharge or knockout drums, discussed below with reference to FIG. 2, and the intercoolers. The heavier wash oils are preferred for washing the compressors.

In another embodiment, a heavy hydrocarbon stream from the separation system of the MTO reaction system is used as the contaminant-removal medium. In this embodiment, for example, the contaminant-removal medium comprises a C4+ hydrocarbon fraction, a C5+ hydrocarbon fraction, or a C6+ hydrocarbon fraction.

In another embodiment, the contaminant-removal medium can be provided as a byproduct of an MTO reaction system. For example, in one embodiment, the contaminant-removal medium comprises at least a portion of a Quench Tower bottoms stream from an MTO separation system. It has been discovered that a heavy aromatic oil comprising aromatic compounds can be isolated from an MTO Quench Tower bottoms stream. This heavy aromatic oil is produced in the MTO reaction system and has desirable properties as a compressor or intercooler wash oil. The heavy aromatic oil will condense in the Quench Tower as well as in the first stage discharge or knockout drum, discussed below. In order to recover the heavy aromatic oil, a bottom skim preferably is provided for decanting the oil off the top of the condensed water from the Quench Tower and/or discharge or knockout drum. The skimmed oil is sent to a settling device such as a drum or any device that provides settling time and an interface from which to withdraw the oil. The withdrawn heavy aromatic oil is then collected and stored in a separate tank where it could be used for injection, preferably intermittent injection, into the process gas compressor or intercooler. Alternatively, the heavy aromatic oil can be separated from the other components in the Quench Tower bottoms stream through a well-known separation technique, e.g., distillation, and advantageously recycled to one or more compressors or intercoolers as the contaminant-removal medium.

The flow rate of the contaminant-removal medium into a given compressor or intercooler may vary based on a variety of factors such as product fraction flow rate through the compressor(s) and operating temperatures. A portion of the contaminant-removal medium may vaporize as it is injected into the compressors. Vaporization is undesirable as the contaminant-removal properties of the contaminant-removal medium are reduced if the medium is in the vapor phase. Thus, the injection rate of the contaminant-removal medium preferably is selected so that at least a portion of the contaminant-removal medium is in the liquid phase after it is injected into the compressors, thereby providing a contaminant wash within the compressor volume.

As indicated above, as compressor fouling develops, the fouled compressor body will begin vibrating. This fouling, if left uncorrected, can lead to compressor inefficiency and, ultimately, to compressor failure. In one particularly desirable embodiment of the present invention, the vibrations of one or more of the compressors are monitored either by a vibration detection device or by less sophisticated means, e.g., an individual feeling the outer surface of the compressor or listening for vibrational noises. In this embodiment, as vibrations are detected, the contaminant-removal medium is intermittently injected into the compressor on an as-needed basis. The intermittent compressing preferably is responsive to a determination in the monitoring that the vibration in the compressor has exceeded a predetermined vibration ceiling.

In another embodiment, the contaminant-removal medium injection system can inject contaminant-removal medium into the compressor or intercooler at prescheduled intervals. The interval between injections may vary based on a number of factors. Desirably, in a continuously operating MTO separation system, the contaminant-removal medium is injected into the initial compressor, which receives the overhead stream from a Quench Tower, or into an intercooler, at a rate of at least one injection every two months, at least one injection per month, at least one injection per week, at least two injections per week, or at least one injection per day. In other embodiments, the interval between injections is 12 hours, 6 hours, 3 hours or 1 hour. To facilitate intermittent contaminant-removal medium injection, in one embodiment, a timer is implemented to cause the contaminant-removal medium injection apparatus to inject the contaminant-removal medium into the compressor or intercooler at predetermined intervals. In a third embodiment, the injection system continuously injects contaminant-removal medium into the one or more compressors and/or intercoolers. However, it is preferable to use intermittent injections since the injections reduce compressor capacity, the loads on the wash oil separation equipment, and wash oil costs.

The length of each injection period, e.g., the duration of each injection, also can vary based on a variety of factors. Typically, the contaminant-removal medium is injected into one or more compressors and/or intercoolers for at least 6 hours, more preferably for at least 10 hours, and most preferably for at least 14 hours. In terms of ranges, each injection period can be from 1 to 24 hours, more preferably from 5 to 14 hours, and most preferably from 8 to 14 hours.

Prior to injection into the one or more compressors and/or intercoolers, the contaminant-removal medium is preferably stored in a contaminant-removal medium storage tank which is in fluid communication with a pump that pumps the contaminant-removal medium to one or more stages or sections of the compressor(s), to the inlet of the compressor, and/or to one or more intercoolers.

The present invention is also directed to an improved compressor for use in an MTO separation system. The compressor includes a compressor housing having an inlet for receiving an effluent to be compressed, e.g., from an MTO Quench Tower overhead stream. Optionally, the compressor inlet is in fluid communication with a reactor outlet. The compressor housing also provides a compressor outlet. A compressing mechanism within the compressor housing acts to compress the effluent. Preferably, the compressing mechanism includes an impeller rotatable about a longitudinal axis, diaphragms separating an impeller from an adjacent impeller, and a labyrinth or channel oriented between the impeller and the diaphragms given section. In one embodiment, the compressor includes a plurality of impellers, each having an associated pair of diaphragms which provide the labyrinth or channel. The compressor also includes an injection unit having a nozzle for injecting a deposit-removal medium into the compressor housing adjacent the labyrinth or channels of a compressor section. The present invention preferably is implemented in a continuous-flow compressor, such as a centrifugal compressor. Optionally, the present invention is implemented in an axial or screw compressor, although the amount of liquids injected into these types of compressors should be carefully monitored and minimized in order to maintain compressor integrity.

The compressor optionally includes a vibration detector, as discussed above, which is adapted to detect impeller vibrations. The vibration detector includes a determination unit for determining whether the vibrations have exceeded a predetermined vibration ceiling. Preferably, the injection unit intermittently injects the deposit-removal medium into the compressor housing responsive to a determination by the determination unit that the vibrations have exceeded a predetermined vibration ceiling. Alternatively, the injection unit intermittently injects the deposit-removal medium into the compressor housing responsive to a user determining that the vibrations have exceeded a predetermined vibration ceiling, and the user activating the injection unit.

Preferably, one or more injection ports are provided in the wall of the compressor body, each port preferably being oriented adjacent a respective compressor section. Each injection port receives an injection nozzle which injects the deposit-removal medium directly into the channel of a respective compressor section. Preferably, the injection unit directly injects the deposit-removal medium into each channel of a given compressor stage. Optionally, a plurality of ports are associated with a single channel of a compressor section. In this embodiment, a plurality of nozzles inject the deposit-removal medium into the single channel.

In another embodiment, the compressor is coupled to a compressor intercooler in fluid communication with the outlet thereof. An intercooler injection unit injects the deposit-removal medium into the intercooler. The injection unit preferably injects the deposit-removal medium into the compressor inlet.

FIG. 1 illustrates one MTO separation system implementing compressors in accordance with the present invention. A heated methanol-containing feedstock 100 is directed to a reactor 102. In the reactor 102, the methanol contacts a catalyst, preferably a molecular sieve catalyst, under conditions effective to convert the methanol to a product effluent comprising light olefins, which exits the reactor through oxygenate conversion product effluent line 104 and, after optionally being cooled in one or more heat exchangers, not shown, is directed to Quench Tower 106. In the Quench Tower, the product effluent contacts directly with a quench medium, e.g., water, at an initial temperature over a series of suitable contacting devices. The amount of quench medium needed in Quench Tower 106 is dictated by a number of factors, including, but not necessarily limited to the composition of the quench medium, the temperature of quench medium recycle introduced to the Quench Tower through recycle line 110, and desired temperature differences and pressure differences between the various streams. The gaseous products are separated as overhead or light product fraction stream 112. The heavy product fraction stream 108, which exits from the bottom of the Quench Tower 106 at an exiting temperature, comprises the bulk of byproduct water, a portion of the unreacted oxygenate feedstock (except those oxygenates that are gaseous under the quenching conditions), a small portion of the oxygenate conversion byproducts, particularly heavy hydrocarbons (C5+), and usually the bulk of the quench medium.

A preferred quench medium is water, which is for all intents and purposes indistinguishable from byproduct water. This eliminates the need for steps to separate the quench medium from byproduct water in the heavy product fraction. In the event that a quench medium other than water is used and this quench material is substantially in a liquid form under quenching conditions, heavy product fraction 108, or any, or all of the several fraction into which the heavy product fraction is divided may be processed to separate the quench medium from byproduct water. For example, if the quench medium is a high boiling hydrocarbon such as diesel fuel or similar stream, it is immiscible with byproduct water. Such a quench medium is separated by a properly designed weir system in the bottom of Quench Tower 106, or in a drum separator or other separation device at many different points of the process in the present invention. Further, if any heavy hydrocarbons ($C_5+$) are formed in the oxygenate conversion reaction, they also may be removed from byproduct water in stream 108 or other points in the process in substantially the same manner as or along with the removal of the quench medium. If the quench medium is a relatively light material, which is substantially gaseous under the quenching conditions, and hence being present in substantial quantities in the light product fraction, such a quench medium can be separated in downstream olefin recovery processes encompassing the entire oxygenate conversion and olefin recovery and purification process.

Light product fraction stream 112 is directed to one or more compressor bodies 114, wherein the light product fraction is compressed or pressurized. Applicants have discovered that compressor fouling is particularly an issue in the initial stages of the first compressor body that receives the overhead stream from the Quench Tower. That is, compressor fouling is particularly a problem in the first stage of the first compressor body that the light product fraction 112 enters. Compressor fouling is not as significant of a problem in subsequent compressor stages. The compression ratios of the one or more compressor bodies can vary widely as disclosed, for example, by U.S. Pat. No. 6,441,261 to Kuechler et al., the entirety of which is incorporated herein by reference.

In one embodiment, at least a portion of the cooled olefin product stream from an MTO separation system is compressed in one or more compressors comprising one to four stages with cooling of the material between the stages (intercooling), wherein each of the compressors preferably has a compression ratio of between about 1.4 and about 6.0, desirably between about 1.7 and about 4.0, and, more desirably, between about 2.0 and about 3.5. By compression ratio is meant the value of the absolute pressure at the outlet of a given stage of the compression system divided by the absolute pressure at the inlet of that same stage. Higher compression ratios are generally desirable, and obtainable in accordance with the present invention, in that they result in less expensive compression systems, although much higher compression ratios are generally limited by the level of fouling contaminants in the cooled olefin product stream. Compression system inlet pressures preferably range from about 2 psig (13.8 kPag) to about 50 psig (344.7 kPag), more preferably between about 5 psig (34.5 kPag) to about 20 psig (137.9 kPag).

The compressed product is preferably directed to one or more intercoolers and discharge drums (see FIG. 2) for initial product separation. Compressed product fraction 116 exits the one or more compressor bodies 114 and is directed to a separation unit 118, which may include one or more separation units, e.g., distillation towers, splitters, wash units, etc. In separation unit 118, byproducts and generally undesirable components, e.g., oxygenate contaminants, from the compressed product fraction 116 are removed through one or more bottoms streams, illustrated in FIG. 1 generally as line 122. Overhead stream 124 comprising substantially pure ethylene and/or propylene is then optionally directed to one or more secondary compressors 132, which form a final condensed product stream. Applicants have discovered that compressor fouling is not a significant problem in these secondary compressors, although the injection of a contaminant-removal medium in these one or more compressors or other MTO separation system compressors is within the scope of the present invention.

FIG. 2 illustrates a contaminant-removal medium injection system in accordance with one embodiment of the present invention. Light product fraction stream 112 from FIG. 1, or any other separation system, is shown entering compressor 114 via compressor inlet 254. FIG. 2 illustrates a centrifugal compressor, although any of a variety of compressors may be implemented in accordance with the present invention. In the centrifugal compressor illustrated, axle 224 spins about its longitudinal axis causing compressor wheels or impellers 226 to spin about the axis and compress stream 112. Compressed stream 232 then exits the compressor through outlet 230. The operation of centrifugal compressors is well known in the art and will not be described in further detail herein.

Although four sections, each defined by a pair of walls or diaphragms 222 and an impeller 226, are illustrated in the single compressor body 114 of FIG. 2, any number of stages or sections may be implemented in a given compressor body. For example, an MTO compressor may include 2, 3, 4 or more stages in a given compressor body, each stage having from 1 to 7 sections. Similarly, any number of compressor bodies, in series or in parallel, can be implemented in accordance with the present invention. Preferably, fewer than 4 or 3 compressor bodies are implemented between the Quench Tower 106 and separation system 118.

A typical contaminant removal system, illustrated in FIG. 2, includes a contaminant-removal tank 202, which holds the contaminant-removal medium. The tank 202 includes an outlet line 204 through which the contaminant-removal medium exits the tank. Line 204 is directed to pump 206 that pumps the contaminant-removal medium through pressurized line 208 and line 212. Overall flow control can be accomplished by changing the speed of the pump or displacement of the pump. Pump 206, in one embodiment, is a positive displacement pump. Optionally, a wash oil screen, e.g., 80 mesh screen, is used on the discharge of the pump to trap foreign matter. A first portion of the contaminant-removal medium can be directed through line 212 back to the tank via a pressure control valve 210. This valve 210 controls the operating pressure of the system. The second portion of the flow is directed to line 208 where optionally the total flow to the injection system is controlled by a flow control device, not shown, located in line 208. The flow control device in line 208 can a ball valve, needle valve, gate valve, plug valve, block valve, slide valve or any other control device known to be suitable for control of fluids at the rates and pressures required by the compressor and auxiliaries. A second portion of contaminant-removal medium from line 208 is directed through line 214 and is divided between individual section introduction lines 216, which direct the contaminant-removal medium preferably to each of the sections of the compressor body 114.

In one embodiment, the contaminant-removal medium is directed through a single individual section introduction line and only to the first section of a compressor stage. Alternatively, the contaminant-removal medium is directed through a single individual section introduction line and only to the second section of the compressor stage. Similarly, the contaminant-removal medium, in another embodiment, is directed through a single individual section introduction line to any one or more of the third through tenth (or more) sections of the compressor stage. More preferably, however, the contaminant-removal medium is directed to each of the sections of a given compressor stage, as shown in FIG. 2, wherein the contaminant-removal medium is directed to each of the four sections in the compressor stage shown in compressor body 114. If the contaminant-removal medium is directed to fewer than all of the sections of a given compressor stage, it is preferred that the contaminant-removal medium is directed to the first section, more preferably to the first and second sections, more preferably to the first through third sections, and so on, incrementally to however many sections exist in a given compressor stage. Similarly, if the contaminant-removal medium is directed to fewer than all of the stages of a given compressor system (which may include one or more compressor bodies), it is preferred that the contaminant-removal medium is directed at least to the first stage, more preferably at least to the first and second stages, more preferably at least to the first through third stages, and so on, incrementally to however many stages exist.

Each of lines 216 preferably includes a flow control device 218, as described above. Optionally, a portion of the contaminant-removal medium in line 214 is directed through line 256 to one or more additional compressors, not shown, in the MTO compressor system. Line 256 also preferably includes a flow control device, not shown. Similarly, at least a portion of the contaminant-removal medium in line 214 optionally is directed through line 246 to the compressor inlet 254. In this embodiment line 246 may enter the side of the inlet 254 through a hole as shown in FIG. 2, or line 246 can feed the contaminant-removal medium directly into inlet 254, as described above. In another embodiment, contaminant-removal medium is injected into stream 112 prior to introduction into inlet 254. Line 246 also preferably includes a flow control device 244.

After being compressed in compressor body 114, the compressed stream 232 can be directed to an intercooler 234 via intercooler inlet 252. The contaminant-removal medium also may be directed to the compressor intercooler 234 as shown by line 248, which optionally includes a flow control device 250. Line 248 can be directed to intercooler inlet 252 as shown in FIG. 2, or to the interior of the intercooler 234 via a nozzle placed in a hole provided in the side of intercooler 234. In the intercooler, compressed stream 232 is cooled by a cooling medium. Additionally, in the intercooler the compressed stream 232 optionally contacts the contaminant-removal medium under conditions effective to remove fouling contaminants from the interior surfaces thereof and thereby forming a mobile contaminant that is easily removed from the intercooler through cooled stream 236 that exits the intercooler 234 and enters a separation unit 238, such as a discharge drum or knockout drum, for further processing. Separation unit 238 separates the cooled stream 236 into compressed product fraction 116 comprising light olefins, which optionally is directed to one or more additional compressor bodies and/or intercoolers as well as to separation system 118 for further processing as shown in FIG. 1, and a condensed stream 242 which preferably includes the contaminant-removal medium as well as any contaminants dissolved therein and/or removed thereby. The condensed stream 242, or a portion thereof, optionally is redirected to the Quench Tower 106 where it can serve as the quench medium. The injection system illustrated in FIG. 2 is one non-limiting embodiment of the present invention, and many other possible injection system configurations exist in accordance with the present invention.

As discussed above, the present contaminant removal process is particularly suited for use in compressors and/or intercoolers in an MTO separation system. Preferably, the conditions in the MTO reactor including the pressure, temperature, weight hourly space velocity (WHSV), etc., are conducive to converting the methanol to light olefins, as discussed in more detail hereinafter.

Typically, molecular sieve catalysts have been used to convert oxygenate compounds to light olefins. Silicoaluminophosphate (SAPO) molecular sieve catalysts are particularly desirable in such a conversion process, because they are highly selective in the formation of ethylene and propylene.

The feedstock preferably contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve catalyst composition into one or more olefins, preferably and predominantly, ethylene and/or propylene, often referred to as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol, dimethyl ether, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

Having now fully described the invention, it will be appreciated by those skilled in the art that the invention can be performed within a wide range of parameters within what is claimed, without departing from the spirit and scope of the invention.

What is claimed is:

1. A process for removing contaminants from a continuous flow compressor in a methanol to olefin separation system, the process comprising the steps of:
   (a) compressing an effluent in the compressor, the compressor having an inlet and an outlet and an inner compressor surface, the compressing occurring under conditions effective to form a contaminant on the inner compressor surface;
   (b) injecting a contaminant-removal medium into the compressor;
   (c) contacting the contaminant-removal medium with the contaminant under conditions effective to remove the contaminant from the inner compressor surface thereby forming a mobile contaminant; and
   (d) removing the mobile contaminant from the compressor wherein the continuous flow compressor comprises at least one compression stage, the at least one compression stage comprising a plurality of sections, and wherein the injecting comprises injecting the contaminant-removal medium into the plurality of sections of the at least one compression stage.

2. The process of claim 1 wherein the contaminant-removal medium comprises water.

3. The process of claim 1 wherein the contaminant-removal medium contains substantially no sulfur.

4. The process of claim 1 wherein the contaminant-removal medium comprises a $C_5+$ hydrocarbon fraction.

5. The process of claim 1 wherein the injecting is performed continuously.

6. The process of claim 1 wherein the injecting is performed intermittently.

7. The process of claim 1 wherein the process further comprises the step of:
   (e) injecting the contaminant-removal medium into a compressor intercooler.

8. The process of claim 1 wherein the contaminant-removal medium mixes with the effluent after the injecting, the process further comprising the step of:
   (e) separating the contaminant-removal medium from the effluent.

9. The process of claim 1 wherein the contaminant removal medium is injected into the inlet of the compressor.

10. The process of claim 1 wherein the continuous-flow compressor is an axial flow compressor.

11. The process of claim 1 wherein the continuous-flow compressor is a screw compressor.

12. The process of claim 1 wherein the continuous-flow compressor is a centrifugal compressor.

13. The process of claim 1 wherein the contaminant-removal medium comprises at least one aromatic compound.

14. The process of claim 1 wherein the contaminant-removal medium comprises at least 50 weight percent aromatic components based on the total weight of the contaminant removal medium.

15. The process of claim 14 wherein the contaminant-removal medium comprises at least 70 weight percent aromatic compounds based on the total weight of the contaminant removal medium.

16. The process of claim 15 wherein the contaminant-removal medium comprises at least 90 weight percent aromatic compounds based on the total weight of the contaminant removal medium.

17. A process for removing contaminants from a compressor in a methanol to olefin separation system, the process comprising the steps of:
   (a) compressing an effluent in the compressor, the compressor having an inlet and an outlet and an inner compressor surface, the compressing occurring under conditions effective to form a contaminant on the inner compressor surface, wherein the contaminant causes a vibration in the compressor;
   (b) injecting a contaminant-removal medium into the compressor;
   (c) contacting the contaminant-removal medium with the contaminant under conditions effective to remove the contaminant from the inner compressor surface thereby forming a mobile contaminant;
   (d) removing the mobile contaminant from the compressor; and
   (e) monitoring the vibration.

18. The process of claim 17 wherein the injecting is performed in response to the vibration in the compressor.

19. The process of claim 17 wherein the effluent comprises a hydrocarbon selected from the group consisting of butadiene, pentadiene, cyclopentadiene, hexadiene, cyclohexadiene, $C_7+$ dienes, styrene, $C_4+$ styrenic compounds, and mixtures thereof.

20. A process for removing contaminants from a compressor in a methanol to olefin separation system, the process comprising the steps of:
   (a) compressing an effluent in the compressor, the compressor having an inlet and an outlet and an inner compressor surface, the compressing occurring under conditions effective to form a contaminant on the inner compressor surface;
   (b) injecting a contaminant-removal medium into the compressor, wherein the contaminant-removal medium comprises at least a portion of a Quench Tower bottoms stream, wherein the Quench Tower is part of the methanol to olefin separation systems;
   (c) contacting the contaminant-removal medium with the contaminant under conditions effective to remove the contaminant from the inner compressor surface thereby forming a mobile contaminant; and
   (d) removing the mobile contaminant from the compressor.

21. A process for removing contaminants from a compressor in a methanol to olefin separation system, the process comprising the steps of:
   (a) contacting a methanol to olefin product fraction with a quenching medium in a Quench Tower under conditions effective to form a Quench Tower overhead stream and a Quench Tower bottoms stream, wherein the Quench Tower overhead stream comprises light olefins, and wherein the Quench Tower bottoms steam comprises spent quench medium and a wash oil;
   (b) separating the wash oil from the spent quench medium by skimming the oil from the spent quench medium;
   (c) injecting the wash oil into a compressor to remove contaminant from the compressor, thereby forming a mobile contaminant; and
   (d) removing the mobile contaminant from the compressor.

22. A process for removing contaminants from a compressor in a methanol-to-olefin separation system, the process comprising the steps of:
   (a) compressing an effluent in a first compressor stage to form a compressed effluent, the first compressor stage having a first inlet, a first outlet and a first inner compressor surface, wherein the first compressor stage is in the compressor, and wherein the compressing occurs under conditions effective to form a contaminant on the first inner compressor surface;
(b) injecting a contaminant-removal medium into the first compressor stage;
(c) contacting the contaminant-removal medium with the contaminant under conditions effective to remove the contaminant from the first inner compressor surface thereby forming a mobile contaminant;
(d) removing the mobile contaminant from the first compressor stage; and
(e) compressing the compressed effluent in a second compressor stage, the second compressor stage having a second inlet, a second outlet and a second inner compressor surface.

23. The process of claim 22 wherein the first compressor stage and the second compressor stage are in a single compressor body.

24. The process of claim 22 wherein the first compressor stage and the second compressor stage are in separate compressor bodies.

25. The process of claim 22 wherein step (e) occurs before step (d).

26. The process of claim 22 wherein the contaminant-removal medium comprises water.

27. The process of claim 22 wherein the contaminant-removal medium contains substantially no sulfur.

28. The process of claim 22 wherein the contaminant-removal medium comprises a $C_5+$ hydrocarbon fraction.

29. The process of claim 22 wherein the injecting is performed continuously.

30. The process of claim 22 wherein the injecting is performed intermittently.

31. A process for removing contaminants from a compressor in a methanol-to-olefin separation system, the process comprising the steps of:
(a) compressing an effluent in a first compressor stage to form a compressed effluent, the first compressor stage having a first inlet, a first outlet and a first inner compressor surface, wherein the first compressor stage is in the compressor, and wherein the compressing occurs under conditions effective to form a contaminant on the first inner compressor surface;
(b) injecting a contaminant-removal medium into the first compressor stage;
(c) contacting the contaminant-removal medium with the contaminant under conditions effective to remove the contaminant from the first inner compressor surface thereby forming a mobile contaminant;
(d) removing the mobile contaminant from the first compressor stage; and
(e) injecting the contaminant-removal medium into a compressor intercooler.

32. The process of claim 31 wherein the contaminant-removal medium is injected into the first inlet.

33. The process of claim 31 wherein the contaminant comprises an aromatic compound.

34. The process of claim 31 wherein the compressor is a continuous-flow compressor.

35. The process of claim 34 wherein the continuous-flow compressor is a centrifugal compressor.

36. The process of claim 34 wherein the contaminant-removal medium comprises at least one aromatic compound.

37. A process for removing contaminants from a continuous-flow compressor in a methanol-to-olefin separation system, the process comprising the steps of:
(a) compressing an effluent in a first compressor stage to form a compressed effluent, the first compressor stage having a first inlet, a first outlet and a first inner compressor surface, wherein the first compressor stage is in the compressor, and wherein the compressing occurs under conditions effective to form a contaminant on the first inner compressor surface;
(b) injecting a contaminant-removal medium into the first compressor stage;
(c) contacting the contaminant-removal medium with the contaminant under conditions effective to remove the contaminant from the first inner compressor surface thereby forming a mobile contaminant;
(d) removing the mobile contaminant from the first compressor stage, wherein the first compressor stage is in the continuous flow compressor, and wherein the first compressor stage comprises a plurality of sections, and the injecting comprises injecting the contaminant-removal medium into the plurality of sections of the first compressor stage.

38. The process of claim 37 wherein the contaminant-removal medium comprises at least 50 weight percent aromatic components based on the total weight of the contaminant-removal medium.

39. The process of claim 38 wherein the contaminant-removal medium comprises at least 70 weight percent aromatic compounds based on the total weight of the contaminant-removal medium.

40. The process of claim 39 wherein the contaminant-removal medium comprises at least 90 weight percent aromatic compounds based on the total weight of the contaminant-removal medium.

41. A process for removing contaminants from a compressor in a methanol-to-olefin separation system, the process comprising the steps of:
(a) compressing an effluent in a first compressor stage to form a compressed effluent, the first compressor stage having a first inlet, a first outlet and a first inner compressor surface, wherein the first compressor stage is in the compressor, and wherein the compressing occurs under conditions effective to form a contaminant on the first inner compressor surface;
(b) injecting a contaminant-removal medium into the first compressor stage;
(c) contacting the contaminant-removal medium with the contaminant under conditions effective to remove the contaminant from the first inner compressor surface thereby forming a mobile contaminant;
(d) removing the mobile contaminant from the first compressor stage, wherein the contaminant causes a vibration in the compressor; and
(e) monitoring the vibration.

42. The process of claim 41 wherein the injecting is performed in response to the vibration in the compressor.

43. The process of claim 41 wherein the effluent comprises a hydrocarbon selected from the group consisting of butadiene, pentadiene, cyclopentadiene, hexadiene, cyclohexadiene, $C_7+$ dienes, styrene, $C_4+$ styrenic compounds, and mixtures thereof.

44. The process of claim 41 wherein the contaminant-removal medium comprises at least a portion of a Quench Tower bottoms stream, wherein the Quench Tower is part of the methanol-to-olefin separation system.

* * * * *